United States Patent
Beaulieu et al.

(10) Patent No.: US 9,026,395 B2
(45) Date of Patent: May 5, 2015

(54) SPECIFIC GRAVITY MEASURING TOOL

(76) Inventors: Kelly Beaulieu, Portage la Prairie (CA); Philip Maurice Church, Stittsville (CA)

( * ) Notice: Subject to any disclaimer, the term of this patent is extended or adjusted under 35 U.S.C. 154(b) by 1228 days.

(21) Appl. No.: 12/675,866

(22) PCT Filed: Aug. 26, 2008

(86) PCT No.: PCT/CA2008/001493
§ 371 (c)(1), (2), (4) Date: Sep. 9, 2010

(87) PCT Pub. No.: WO2009/026684
PCT Pub. Date: Mar. 5, 2009

(65) Prior Publication Data
US 2010/0332178 A1    Dec. 30, 2010

Related U.S. Application Data

(60) Provisional application No. 60/968,209, filed on Aug. 27, 2007.

(51) Int. Cl.
| | |
|---|---|
| *G01N 9/36* | (2006.01) |
| *G01N 9/00* | (2006.01) |
| *G01N 27/00* | (2006.01) |
| *G01N 33/02* | (2006.01) |
| *G01N 27/02* | (2006.01) |

(52) U.S. Cl.
CPC ............. *G01N 9/36* (2013.01); *G01N 33/025* (2013.01); *G01N 27/02* (2013.01)

(58) Field of Classification Search
USPC .......... 702/127, 137, 189; 73/32 R; 324/71.1
See application file for complete search history.

(56) References Cited

U.S. PATENT DOCUMENTS

| | | |
|---|---|---|
| 6,147,503 A | 11/2000 | Nelson et al. |
| 6,340,892 B1 | 1/2002 | Rynhart et al. |
| 6,691,563 B1 | 2/2004 | Trabelsi et al. |
| 6,784,672 B2 | 8/2004 | Steele et al. |
| 2003/0135336 A1* | 7/2003 | Inoue et al. .................. 702/57 |

(Continued)

OTHER PUBLICATIONS

Dahms et al., Correlation of Percent Body Fat with Body Specific Gravity in Rats, The Journal of Nutrition—American Institute of Nutrition, May 21, 1982, pp. 398-400.*
http://www.your dictionary.com/biotype p. 4 citing American Heritage Medical dictionary http://medical.yourdictionary.com/.*

(Continued)

*Primary Examiner* — Janet Suglo
*Assistant Examiner* — L. Anderson
(74) *Attorney, Agent, or Firm* — Ryan W. Dupuis; Kyle R. Satterthwaite; Ade & Company Inc.

(57) ABSTRACT

A specific gravity measuring tool comprises a portable handheld housing supporting a plurality of electrodes at a fixed known spacing thereon and a display for displaying a determined specific gravity thereon. The electrodes are arranged to be penetrated into the object to be measured, for example a potato. The electrodes include a first pair across which an electrical potential is arranged to be generated, and a second pair across which an electrical potential is arranged to be sensed. A processor of the tool is arranged to calculate electrical impedance using the electrical potential generated across said first pair of the electrodes, the electrical potential sensed at said second pair of electrodes, and the known spacing between the electrodes so that the specific gravity can be determined using a predetermined relationship between electrical impedance and specific gravity.

12 Claims, 1 Drawing Sheet

(56) References Cited

U.S. PATENT DOCUMENTS

2009/0192404 A1* 7/2009 Ortiz et al. .................. 600/547
2010/0039127 A1* 2/2010 Orazem ....................... 324/718

OTHER PUBLICATIONS

Stuart O. Nelson, Dielectric Properties of Agricultural Products: Measurement and Applications: IEEE Transactions on Electrical Insulation; vol. 26, No. 4 Oct. 1991.

* cited by examiner

SPECIFIC GRAVITY MEASURING TOOL

This application claims priority from U.S. provisional application Ser. No. 60/968,209, filed Aug. 27, 2007.

FIELD OF THE INVENTION

The present invention relates to a portable tool for measuring specific gravity of an object, and more particularly relates to a method and a system of determining the specific gravity of fruit and vegetables, for example whole potato tubers, tomatoes, apples, melons etc. In one application, the tool will allow for the sampling of whole potato tubers prior to digging all of them out of the field, sampling of tubers during storage and the sampling of tubers at delivery to the end user prior to placing them on the processing line.

BACKGROUND

Specific gravity of the solids content of potatoes is an important determinant of harvest quality. A processing potato must have a high specific gravity and low sugar content. A high specific gravity results in French fries that have a more desirable mealy texture and flavour, are crisp and absorb less oil during frying compared to fries from potatoes with a lower dry matter content. Determining the specific gravity is necessary because it indicates how much water must be evaporated from the potato during the dehydration process prior to frying the strips. It is actually a measure of the dry matter or "solids" in the potato. High specific gravity potatoes make the best French fries and dehydrated potato products. In practice, this attribute of a tuber is an indicator of maturation that the industry uses as a reference to judge fry quality, baking characteristics and storability. More importantly the specific gravity measurements reflect environmental factors and cultural management procedures that were made during the production season. In addition, the distribution of starch or dry matter, sugar content, types of sugars and distribution, internal cell structures, tuber size and shape, tuber defects such as growth cracks and hollow heart can also influence specific gravity measurements. Given these variations there is a definite need to determine and assess specific gravity. Current methods of specific gravity determination are inaccurate and time-consuming. Improper sampling and methods of determinations could mislead specific gravity measurements and result in improper equipment settings on the processing line. This results in very expensive product quality losses for the processor. Specific gravity is a determinant used by food processors to pay farmers for their crops. Accurate measurement of specific gravity is therefore required to ensure fair market value.

There is no product or device in existence that can perform automatic monitoring of specific gravity. Specific gravity is currently determined by a crude manual method. A sample of tubers and several tubs of water (with salt added to make brine at different specific gravities) are used. The weight in air versus the weight in water method is one of the common methods of specific gravity determinations. Selected sample units are first weighed in air and then the same unit is re-weighed suspended in water. Specific gravity can then be calculated using the following formula:

Specific gravity=Weight in air/(Weight in air−Weight in water)

This is a time-consuming testing method that does not allow for quick and accurate sampling and therefore it does not allow the processor to set the fryers and drier machines in real time. This sampling method is also not very accurate as contamination of the brine barrel with dirt, potato starch etc. occurs after only a few samples have been tested.

The other common method of measuring specific gravity is to use a potato hydrometer. The hydrometer consists of a float with the neck graduated to specific gravity readings. A basket containing the sample is hung beneath the float and the whole assembly placed in water. After some time the float remains steady and the specific gravity is read from where the water level is on the neck of the hydrometer. The higher the specific gravity, the deeper the hydrometer will be in the water.

The disadvantage of this method is that the hydrometer is calibrated to a fixed weight of potatoes in the basket and therefore the sample placed in the basket must be exactly this specified weight.

It can be time-consuming finding tubers of the right size to make the exact weight, and also the hydrometer can bob up and down for some time before a reading can be made. If the hydrometer is knocked about, the chart of specific gravity readings inside the neck can be moved, thereby resulting in totally inaccurate readings. Hence, this method, although commonly used, is not thought to be very accurate. A further disadvantage is the sample size: the hydrometer is limited to the amount specified in the basket and therefore is not a very representative sample.

SUMMARY OF THE INVENTION

According to one aspect of the present invention there is provided a specific gravity tool for measuring specific gravity of an object, the tool comprising:

a plurality of electrodes arranged to contact the object;

a housing arranged to support the electrodes at a known spacing relative to one another;

an electrical potential source arranged to be coupled to a first pair of the electrodes to generate an electrical potential across said first pair of the electrodes;

an electrical potential sensor arranged to be coupled to a second pair of the electrodes different from said first pair of the electrodes and arranged to sense electrical potential across said second pair of the electrodes;

a processor arranged to:
  i) calculate electrical impedance using the electrical potential generated across said first pair of the electrodes by the source, the electrical potential sensed at said second pair of electrodes by the electrical potential sensor, and the known spacing; and
  ii) determine specific gravity using a predetermined relationship between electrical impedance and specific gravity; and a display arranged to display the determined specific gravity.

According to another aspect of the invention there is provided a specific gravity tool for measuring specific gravity of an object, the tool comprising:

a plurality of electrodes arranged to contact the object;

a housing arranged to support the electrodes at a spacing relative to one another;

an electrical current source arranged to be coupled to two of the electrodes to generate an electrical potential across said two of the electrodes;

an electrical potential sensor arranged to be coupled to at least two of the electrodes which are different than the two electrodes used to inject the electrical current;

a controller arranged to:
i) measure the electrical impedance using the electrical potential generated across said two of the electrodes by the source; and
ii) determine specific gravity using a predetermined relationship between electrical impedance and specific gravity of the object being measured; and
a display arranged to display the determined specific gravity for the user.

The predetermined relationship between electrical impedance and specific gravity of the object being measured requires a calibration of the tool and an ability to relate the electrical impedance information to known specific gravity determinations.

Preferably the electrodes each comprise an elongate and rigid penetrating member arranged for penetration into the object arranged to be penetrated into the object at varying depths.

The processor may be arranged to measure plural electrical potentials at the second pair of the electrodes and to calculate an average electrical impedance using the electrical potentials measured at the second pair of the electrodes.

Preferably the housing comprises a handheld housing supporting the display, the electrodes, the electrical potential source, the electrical potential sensor, and the display commonly thereon.

The electrodes may be supported fixed in relation to the housing in which the second pair of the electrodes are spaced apart along an axis extending between the first pair of the electrodes.

The pre-determined relationship between the electrical impedance and specific gravity may comprise test data stored in a memory coupled to the processor which is specific to one or more different biotypes of objects to be measured. When there are plural different biotypes of objects to be measured, the processor is typically arranged to select the test data corresponding to one of the different biotypes prior to the electrodes engaging the object.

The tool is preferably arranged to measure specific gravity of an object of biological origin selected from the group including fruits, vegetables or wood, for example a potato.

The processor is preferably arranged to be coupled to a memory arranged for storing the determined specific gravity of a plurality of different objects contacted by the electrodes. In this instance, the display may be arranged to display only a selected one of the determined specific gravities.

Preferably the processor is arranged to calculate electrical impedance responsive to penetration of the electrodes into the object up to a selected depth.

According to another aspect of the present invention there is provided a method for measuring specific gravity of an object, the method comprising:
providing a housing supporting a plurality of electrodes thereon at a known spacing relative to one another;
contacting the object with the plurality of electrodes;
generating an electrical potential across a first pair of the electrodes;
sensing electrical potential across a second pair of the electrodes;
calculating electrical impedance using the electrical potential generated across said first pair of the electrodes, the electrical potential sensed at said second pair of electrodes, and the known spacing between the electrodes;
determining specific gravity using a predetermined relationship between electrical impedance and specific gravity; and
displaying the determined specific gravity.

The method may include establishing the predetermined relationship between electrical impedance and specific gravity by testing each one of a plurality of different biotypes and storing the results of the testing in the form of test data corresponding to the plurality of different biotypes in a memory. The method may thus further include selecting the test data corresponding to one of the different biotypes prior to the electrodes engaging the object.

The method may further include contacting and determining the specific gravity of a plurality of different objects and storing the determined specific gravities of the different objects in a memory.

The method may also include selecting a depth of penetration of the electrodes into the object and calculating the electrical impedance upon penetration of the electrodes into the object up to the selected depth of penetration.

One embodiment of the invention will now be described in conjunction with the accompanying drawings in which:

BRIEF DESCRIPTION OF THE DRAWINGS

In the drawings like characters of reference indicate corresponding parts in the different figures.

DETAILED DESCRIPTION

Figure 1:
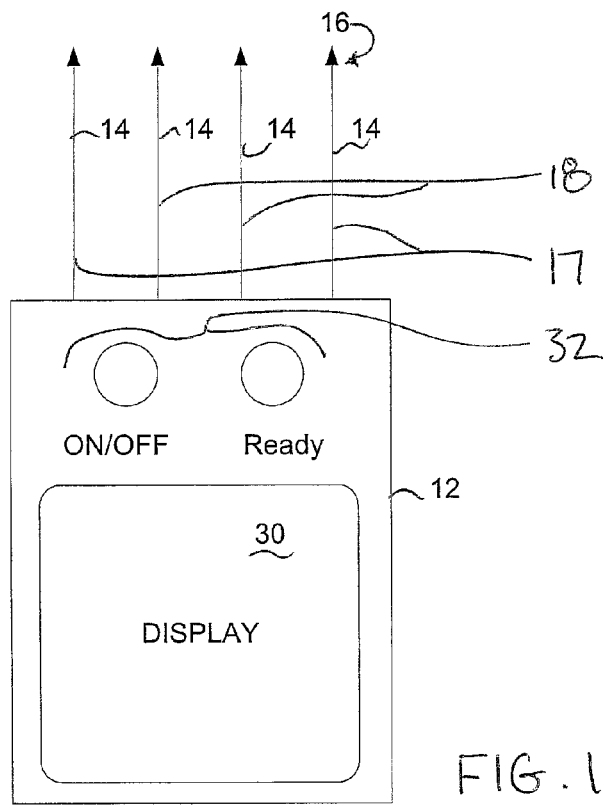
FIG. 1 is a front elevational view of the specific gravity measuring tool.
Figure 2:
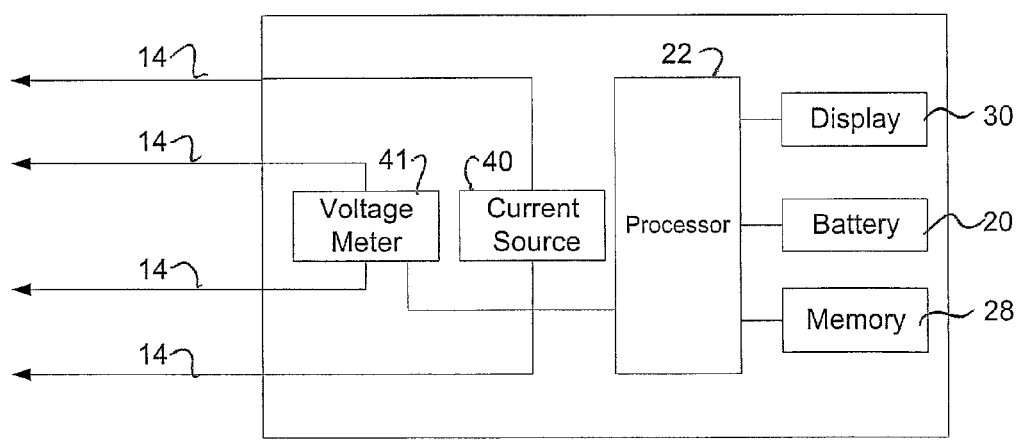
FIG. 2 is a schematic illustration of the working components of the specific gravity measuring tool according to FIG. 1.

Referring to the accompanying figures there is illustrated a tool generally indicated by reference numeral 10. The tool 10 is particularly suited for measuring specific gravity by making use of a correlation between specific gravity and electrical impedance in various tissues, for example tissues of a food object such as a potato.

The tool generally includes a housing 12 which is suitably sized to be handheld and portable. In the illustrated example, the housing supports four electrodes 14 extending outwardly from the housing parallel to one another and at a known spacing therebetween.

Each electrode 14 comprises an elongate penetrating member and includes a pointed free end 16 to assist in penetrating the electrode into the object to be measured. The electrodes 14 are therefore elongate and rigid and fixed relative to one another so as to project outwardly beyond the housing 12.

In some embodiments the electrodes 14 may be supported at an adjustable spacing relative to one another and may be adjustable in length depending upon the object to be measured.

The electrodes are arranged in pairs including an outer first pair 17 of the electrodes 14 and an inner second pair 18 of the electrodes 14. The inner second pair 18 are located at a smaller spacing relative to one another than the outer first pair and are positioned in between the electrodes of the outer pair so as to be evenly spaced apart between the outer pair along an axis extending between the outer pair.

A battery is supported within the housing to act as an electrical power source 20 to supply electrical current as required.

An electrical current source 40 is supported within the housing and is arranged to be coupled to the outer first pair 17 of the electrodes to generate a current and an electrical potential across the first pair 17.

An electrical potential sensor 41 is arranged to be coupled to the inner second pair 18 of the electrodes 14 which are different from the first pair 17. The sensor is arranged to sense electrical potential across the second pair 18 of the electrodes 14.

A processor 22 communicates with the sensor 41 to receive measured data from the sensor 41. The processor 22 also communicates power from the battery 20 to the electrical current source 40 that communicates with the outer first pair of electrodes.

The processor 22 is accordingly arranged to calculate electrical impedance using the electrical potential generated across the first pair of the electrodes by the current source 40, the electrical potential sensed at the second pair of electrodes by the electrical potential sensor 41, and the known spacing between all of the electrodes. The processor also compares the calculated electrical impedence to stored electrical impedence data so that specific gravity can be determined using a predetermined relationship between electrical impedance and specific gravity.

During any given measuring operation, the processor 22 controls the current source 40 to the outer electrode pair 17. An electrical current is thus generated across the two electrodes connected to the electrical source. The electrical potential difference between the electrodes of the inner electrode pair is measured with the sensor 41 which comprises a preamplifier and an Analog-to-Digital converter.

The electrical potential sensed and electrical current applied are recorded by the processor over a period of about 1 second and the electrical impedance is calculated. The processor compares this value to a memory-stored look-up table in the form of data stored in a memory 28 in communication with the processor 22 within the housing. The data stored in the memory comprises a pre-programmed correlation between electrical impedance and specific gravity of the particular object being measured. Accordingly once the electrical impedance is calculated, the specific gravity is determined by comparison to the predetermined relationship between electrical impedance and specific gravity as stored in the memory. The determined specific gravity is then displayed to the user on a suitable numeral display 30 also supported on the housing 12. Accordingly all of the components including the display 30, the electrical current source 40, the processor 22 and the electrodes 14 are all commonly supported on the portable handheld housing 12 as shown in the illustrated embodiment.

The pre-programmed data stored within the memory 28 is specific to each biotype of object to be measured as the correlation between electrical impedance and the specific gravity varies from one biotype of potato to the next for example. These correlations for each biotype must be predetermined with experimental testing and then stored in the memory 28. Each use of the tool thus involves calibrating the tool by initially selecting what biotype of the particular object to be measured is relevant. This ensures that the controller is comparing the calculated impedance to the correct specific gravity values. In the preferred embodiment illustrated herein, various biotypes having test data associated therewith are stored within the memory 28 so that the user must select which data is relevant. Any number and type of specific gravity determination tools can and will be created to determine specific gravity for various fruits and vegetables. Some embodiments of the specific gravity monitoring device will result in destructive sampling of the object being sampled and other embodiments will determine specific gravity without penetration into the body of the fruit or vegetable. This determination will be made by the inventor as determined by the requirements of the end-user.

The computer memory 28 can also be used to store measured values when multiple readings are being taken of several different objects. These stored values can later be recalled to the display by use of keys 32 on the housing which are used to control the various functions of the controller. For comparison purposes, the tool may also include the option of selecting a depth range for the impedance sampling which will affect which electrodes on the penetrating members are connected to the electrical source and sensor circuit respectively depending upon the expected depth of penetration of the penetrating members into the object when the object varies in size.

In use, the user initially inputs into the keys 32 of the tool information relating to the biotype of the potato or object to be measured. Once ready for measurement, the electrodes 14 are then inserted into the object. Upon full insertion the processor begins recording various electrical impedance samples. Once an overall average of electrical impedance is determined, the processor automatically compares this value to stored data which correlates the electrical impedance to the specific gravity of the selected biotype. The measured specific gravity is then displayed to the user on the display 30. Using the keys 32 the user then selects whether the measured value is to be stored in memory or whether a new measurement is to take place.

Electrical impedance is defined as the ratio of the voltage across the element to the current through the element. As described herein, it has been surprisingly discovered that there is a correlation between the electrical impedance of potato tissues and other materials of plant origin and specific gravity and this discovery has been used as a method of stimulating the plant tissues electrically and reading the characteristics of the specific gravity of the whole tuber. This sampling is done destructively, meaning that the skin of the tuber must be penetrated by the electrodes and electrical sensors. Once the skin of the tubers has been penetrated the potato is discarded. Representative samples of tubers should be chosen for testing whether the sampling is being conducted in the field prior to potato harvesting, in the storage facility to determine optimum storage conditions or at the processor in determining the quality of the tubers entering the processing line. The instrument performs bio-impedance spectroscopy analysis and gives a reading of the average specific gravity of the tuber. This information is then used in one of several ways:

1) Field sampling tubers prior to harvest can allow the producer to alter harvest dates, increase irrigation water or determine if the vines should be removed to stop top growth. The specific gravity of potatoes attached to living plants in the field can change rapidly because of water movement into and out of the tubers. When transpiration (water loss through the leaves) exceeds the rate of water absorption by the roots, the vines draw water from the tuber, causing the tuber to decrease in weight, shrink in size, and at that point in time have an increased specific gravity. This process will continue until the leaf cells lose their turgor pressure, the leaves wilt, the stomata close, and photosynthesis ceases or the farmer removes the tops the plants and removes the vines effectively stopping all growth and water movement activity. If the rate of water absorption by the roots exceeds water loss by transpiration, the excess water is pumped into the tubers and they expand, increase in weight, become more brittle, and the specific gravity decreases. The increase in weight of potatoes and decrease in specific gravity, because of absorbed water, are at times sizeable. This effect can also be mitigated by topping the plants or by varying the irrigation water received by the plants prior to harvest. The amount of carbohydrates produced depends upon the rate of photosynthesis and the length of time that it continues. Consequently, there is a direct relationship between length of the growing season and production of high yields of high dry matter content (high specific gravity) potatoes. There is also a direct relationship between high yield and amount of nutrients in a crop. Fertilization may have little direct effect but a large indirect effect on the specific gravity because of the effect of size of the plant on the relative rates of water lost by transpiration and water absorption by the roots. Management of the crop can be more precisely managed if accurate specific gravity sampling is available.

2) In order to improve processing quality of potatoes, it would be advantageous to be able to regulate Dry Matter of tubers during storage. Under normal conditions of storage, moderate to low temperatures and high relative humidity, Dry Matter/Specific Gravity of tubers does not change during several months of storage. However, storage conditions of very high humidity and moderate temperatures can lower Dry Matter/Specific Gravity. Conversely, moderate temperatures and low humidity during storage can increase Dry Matter/Specific Gravity. These changes are caused by a difference in the relative proportion of transpiration and respiration occurring in the tubers and are regulated by the temperature and relative humidity in the storage. Normally, growers will manage their storages to regulate sugar levels, not specific gravity however producers have never had a tool to accurately measure and monitor specific gravity in storage. The feasibility of actually accomplishing this on a commercial scale would need to be evaluated. There may be reluctance on the part of growers to modify their storage conditions because of concerns about increased operating cost, increased weight loss at low humidity or elevated temperatures, and potential disease at high humidity/high temperature conditions. However, by careful control of the storage conditions, some modification in Dry Matter/Specific Gravity may be possible. The storage management practices used to accomplish this may depend on the cultivar and at what stage during the storage period is the adjustment in Dry Matter/Specific Gravity being attempted.

3) Producers delivering potatoes to the processing plant sell their tubers based on quality characteristics as required by the processor and the end product for which the tubers are being purchased. In the case of fry strips, processors prefer to purchase potatoes in the ranges of specific gravity that are best suited to making crisp, light brown fries with a mealy textured interior. Tubers with higher specific gravities results in higher processing yields and less oil uptake during frying. Higher specific gravity tubers also have less variation in sugars than lower specific gravity tubers making them more suitable for processing. Small tubers have a higher specific gravity than larger tubers. It is important for both the producer who is selling the product and the processor who is purchasing it to know the exact specific gravity of the tubers at the time of the sale and delivery to the processing plant. Processors knowing the specific gravity of particular loads of tubers originating from different sources can also better regulate the quality of the product coming out of the processing line by closely matching and planning deliveries of the potatoes.

The proposed concept described herein generally comprises a hand-held device that uses electromagnetic impedance to determine specific gravity of tubers, selected vegetables and fruit and other root crops.

Once the skin of the tubers has been penetrated, the potato is discarded. Common representative sampling methods should be used whether the sampling is being conducted in the field prior to potato harvesting, in the storage facility to determine optimum storage conditions or at the processor in determining the quality of the tubers entering the processing line.

The instrument gives a reading of the average specific gravity of the tuber. A small LED or LCD readout screen mounted on the front of the instrument will give the average specific gravity of the tuber. This reading can be erased or may be logged for future reference. The keypad will allow for data classification by the operator. The reading screen and sensors can be recalibrated by pushing one of the calibration buttons on the face of the instrument. The instrument will be powered by commonly available DC batteries. The instrument will contain a data logger capable of being downloaded into a PC for easy storage of data.

| Functional Characteristics - whole tubers | Benefits |
| --- | --- |
| Bio-impedance is a diagnostic method that takes advantage of the recently discovered relationship between electrical conductivity of biological tissues and the specific gravity of the object being measured | Determination of specific gravity in a rapid and accurate method has long been a sought-after tool in the food processing industry. Other industries that also process biological tissues such as wood products also have a requirement for determining the specific gravity of their raw products. Specific gravity is usually a parameter of the biological tissues that relates directly to the quality of the end-product to the processor. |
| Bio-impedance is a diagnostic method that takes advantage of the passive electrical properties of the biological tissues of the potato | Different tissue properties can be discerned using this method after a standard calibration curve has been established. |
| The equipment and data analyzers required for constructing the bio-impedance specific gravity monitor for tubers is low cost, easily applicable in practice and enables a fast, cheap method of specific gravity determination | The ability to quickly assess specific gravity is a very beneficial advancement for farmers and processors. The ability to make this tool inexpensive and reliable also enables wide distribution and use of this new technology. |

| Functional Characteristics - whole tubers | Benefits |
|---|---|
| The hand held specific gravity monitor gives accurate, instant readings for the tubers and or fruit and vegetable tissues | Knowing specific gravity of tubers and or other fruits & vegetables is important for maximizing profits by both the producer and the processor as it is a quality indicator |
| The specific gravity monitoring tool can be used as another indicator for example in potatoes it will help determine when optimal vine topping and harvesting should occur | Using the specific gravity monitor in the field allows producers to basically set in the best specific gravity they can get by managing the tubers precisely in the final days prior to harvest. Producers will use the tool to determine when to water the plants, when to fertilize and when to best harvest the tubers for maximum economic benefit |
| The SGM will be a useful tool in storage facilities | Although there is only a minimal amount of information currently available about modifying storage conditions to affect specific gravity this new tool can be used to determine optimal conditions. Researcher and farmers can use the tool to determine best management practices for storing tubers |
| The specific gravity monitor allows rapid sampling of large quantities of tubers | Producers and processors can rapidly determine the average specific gravity of a quantity of tubers (a truckload or a bin) and this will help them set prices. |

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A method for measuring specific gravity of a tuber of prescribed biotype, the method comprising:
providing a housing supporting a plurality of electrodes thereon at a known spacing relative to one another;
providing testing derived correlation data which correlates electrical impedance to specific gravity according to the prescribed biotype of the tuber;
contacting the tuber with the plurality of electrodes;
generating an electrical potential across a first pair of the electrodes;
sensing electrical potential across a second pair of the electrodes;
calculating electrical impedance using the electrical potential generated across said first pair of the electrodes, the electrical potential sensed at said second pair of electrodes, and the known spacing between the electrodes;
determining specific gravity using the correlation data which correlates the electrical impedance to the specific gravity; and
displaying the determined specific gravity.

2. The method according to claim 1 including penetrating the electrodes into the tuber.

3. The method according to claim 1 including measuring plural electrical potentials across the second pair of the electrodes and calculating an average electrical impedance using the electrical potentials measured at the second pair of the electrodes.

4. The method according to claim 1 wherein the correlation data relates to a plurality of different biotypes of tubers to be measured, the method including selecting the correlation data corresponding to one of the different biotypes prior to the electrodes engaging the tuber.

5. The method according to claim 1 including contacting and determining the specific gravity of a plurality of different tubers and storing the determined specific gravities of the different tubers in a memory.

6. The method according to claim 1 including selecting a depth of penetration of the electrodes into the tuber and calculating the electrical impedance upon penetration of the electrodes into the tuber up to the selected depth of penetration.

7. A method for measuring specific gravity of a plant tissue of prescribed biotype, the method comprising:
providing a housing supporting a plurality of electrodes thereon at a known spacing relative to one another;
providing testing derived correlation data which correlates electrical impedance to specific gravity according to the prescribed biotype of the plant tissue;
contacting the plant tissue with the plurality of electrodes;
generating an electrical potential across a first pair of the electrodes;
sensing electrical potential across a second pair of the electrodes;
calculating electrical impedance using the electrical potential generated across said first pair of the electrodes, the electrical potential sensed at said second pair of electrodes, and the known spacing between the electrodes;
determining specific gravity using the correlation data according to the prescribed biotype of the plant tissue which correlates the electrical impedance to the specific gravity; and
displaying the determined specific gravity.

8. The method according to claim 7 including penetrating the electrodes into the plant tissue.

9. The method according to claim 7 including measuring plural electrical potentials across the second pair of the electrodes and calculating an average electrical impedance using the electrical potentials measured at the second pair of the electrodes.

10. The method according to claim 7 wherein the correlation data relates to a plurality of different biotypes of plant tissues to be measured, the method including selecting the correlation data corresponding to one of the different biotypes prior to the electrodes engaging the plant tissue.

11. The method according to claim 7 including contacting and determining the specific gravity of a plurality of different plant tissues and storing the determined specific gravities of the different plant tissues in a memory.

12. The method according to claim 7 including selecting a depth of penetration of the electrodes into the plant tissues and calculating the electrical impedance upon penetration of the electrodes into the plant tissues up to the selected depth of penetration.

\* \* \* \* \*